US008952346B2

(12) United States Patent
Dempsey et al.

(10) Patent No.: US 8,952,346 B2
(45) Date of Patent: Feb. 10, 2015

(54) SYSTEMS AND METHODS FOR ISOTOPIC SOURCE EXTERNAL BEAM RADIOTHERAPY

(71) Applicant: ViewRay, Incorporated, Oakwood Village, OH (US)

(72) Inventors: James F. Dempsey, Chagrin Falls, OH (US); Iwan Kawrykow, Sofia (BG)

(73) Assignee: ViewRay Incorporated, Oakwood Village, OH (US)

( * ) Notice: Subject to any disclaimer, the term of this patent is extended or adjusted under 35 U.S.C. 154(b) by 97 days.

(21) Appl. No.: 13/830,794

(22) Filed: Mar. 14, 2013

(65) Prior Publication Data

US 2014/0275696 A1    Sep. 18, 2014

(51) Int. Cl.

| | |
|---|---|
| *G02B 5/00* | (2006.01) |
| *G21K 1/00* | (2006.01) |
| *H01J 1/52* | (2006.01) |
| *H01J 3/00* | (2006.01) |
| *H01J 5/18* | (2006.01) |
| *H01J 29/46* | (2006.01) |
| *A61N 5/10* | (2006.01) |

(52) U.S. Cl.
CPC ............ *A61N 5/1045* (2013.01); *A61N 5/1036* (2013.01); *A61N 5/1071* (2013.01); *A61N 5/1077* (2013.01)
USPC .............. 250/505.1; 250/267; 378/65; 600/1; 600/2; 600/410; 600/411; 600/420

(58) Field of Classification Search
USPC .......... 250/505.1, 267; 378/65; 600/1, 2, 410, 600/411, 420
See application file for complete search history.

(56) References Cited

U.S. PATENT DOCUMENTS

| | | | |
|---|---|---|---|
| 7,907,987 B2 * | 3/2011 | Dempsey | 600/411 |
| 8,190,233 B2 * | 5/2012 | Dempsey | 600/411 |
| 2006/0045238 A1 | 3/2006 | Nguyen | |
| 2008/0063141 A1 | 3/2008 | Luan et al. | |
| 2008/0298550 A1 | 12/2008 | Otto | |

(Continued)

OTHER PUBLICATIONS

Z. Caner Taskin et al., "Optimal Multileaf Collimator Leaf Sequencing in IMRT Treatment Planning", Operations Research, vol. 58, No. 3, May-Jun. 2010, pp. 674-690.

(Continued)

*Primary Examiner* — Jack Berman
*Assistant Examiner* — Meenakshi Sahu
(74) *Attorney, Agent, or Firm* — Mintz Levin Cohn Ferris Glovsky and Popeo, P.C.

(57) ABSTRACT

The subject matter described herein provides methods for developing an IMRT treatment plan for a radiotherapy system. In one aspect, the method can include providing initial treatment parameters. These parameters can include a number of isotopic beams, a transmission angle for each beam, a prescribed dose for a target, and dose volume histogram constraints. The method can further include determining an initial fluence map including one or more beamlets. The initial fluence map can specify a fluence value for each beamlet. The method can further include determining a delivery sequence for the fluence values in the initial fluence map. The delivery sequence can include one or more apertures formed by the leaves of a collimator. These apertures can have a specified size constrained to substantially less than a maximum size associated with the collimator, when the isotopic beam is near a critical structure. Related apparatus and systems are also described.

37 Claims, 5 Drawing Sheets

(56) References Cited

U.S. PATENT DOCUMENTS

2010/0177870 A1     7/2010    Nord et al.
2010/0270480 A1    10/2010    Echner

OTHER PUBLICATIONS

H. Edwin Romeijn et al., "A Column Generation Approach to Radiation Therapy Treatment Planning Using Aperture Modulation", Society for Industrial and Applied Mathematics, 2005, pp. 838-862.

Christopher Fox et al., "Comparative Analysis of 60 Co Intensity-Modulated Radiation Therapy", Physics in Medicine and Biology, 53;IOP Publishing, 2008, pp. 3175-3188.

H. Edwin Romeijn et al., "A Novel Linear Programming Approach to Fluence Map Optimization for Intensity Modulated Radiation Therapy Treatment Planning", Physics in Medicine and Biology, 48;IOP Publishing, 2003, pp. 3521-3542.

International Search Report issued in International Application No. PCT/US2014/023740, mailed Nov. 11, 2014.

\* cited by examiner

FIG. 5

SYSTEMS AND METHODS FOR ISOTOPIC SOURCE EXTERNAL BEAM RADIOTHERAPY

TECHNICAL FIELD

The subject matter described herein relates to the development of a treatment plan for use with an isotopic radiation therapy system.

BACKGROUND

During radiation therapy, beams of radiation can pass through a patient. Because radiation beams can kill cancerous tumors as well as healthy tissue and organs, a treatment plan can be formulated to identify the target to be irradiated, the critical structures to be spared, and the intensity of the radiation beams to be used during treatment. Intensity modulated radiation therapy (IMRT) is a form of therapy that irradiates a patient with one or more beams from a plurality of directions and allows precise control over the delivery of radiation. Radioisotopic therapy units can be used in conjunction with IMRT treatment plans.

SUMMARY

In some implementations, methods and apparatus, including computer program products, and systems are provided for the development of a treatment plan.

In one aspect, one or more initial treatment parameters are provided. The initial treatment parameters are selected from a group consisting of a number of isotopic beams, isocenters for each isotopic beam, a prescribed dose for a target, a maximum dose for a critical structure, and one or more dose volume histogram constraints. In addition, an initial fluence map including one or more beamlets is determined. The initial fluence map specifies a fluence value for each of the one or more beamlets. A delivery sequence for the fluence values in the initial fluence map is determined. The delivery sequence includes one or more apertures formed by a first set of one or more leaves and a second set of one or more leaves in a collimator. The one or more apertures have a specified size constrained to substantially less than a maximum size associated with the collimator, when the isotopic beam is near the critical structure.

The above methods, apparatus, computer program products, and systems can, in some implementations, further include one or more of the following features.

The specified size can be substantially 2 centimeters by 2 centimeters or less.

The delivery sequence can specify a maximum number of apertures or prohibit interdigitation between the first set of one or more leaves and the second set of one or more leaves.

Treatment can begin based on the determined initial fluence map and the determined delivery sequence.

In another aspect, one or more initial treatment parameters are provided. The initial treatment parameters are selected from a group consisting of a number of isotopic beams, isocenters for each isotopic beam, a prescribed dose for a target, a maximum dose for a critical structure, and one or more dose volume histogram constraints. In addition, an initial fluence map including one or more beamlets is determined. The initial fluence map specifies a fluence value for each of the one or more beamlets. A first delivery sequence for the fluence values in the initial fluence map is determined. The first delivery sequence includes one or more apertures formed by a first set of one or more leaves and a second set of one or more leaves in a collimator. One or more dose values are calculated based on the one or more apertures in the first delivery sequence using an a priori dose calculation method. The one or more calculated dose values are compared with the prescribed dose. If there is a significant error between the one or more calculated dose values and the prescribed dose, then a second delivery sequence is determined.

The above methods, apparatus, computer program products, and systems can, in some implementations, further include one or more of the following features.

The second delivery sequence can include one or more apertures formed by the first set of one or more leaves and the second set of one or more leaves. In addition, the one or more apertures in the second delivery sequence can have a specified size constrained to substantially less than a maximum size associated with the collimator, when the isotopic beam is near the critical structure.

The second delivery sequence can further specify a maximum number of apertures or prohibit interdigitation between the first set of one or more leaves and the second set of one or more leaves.

The specified size can be substantially 2 centimeters by 2 centimeters or less.

The a priori dose calculation method can be selected from a group consisting of a Monte Carlo simulation and a discrete ordinates method.

If there is no significant error between the one or more calculated dose values and the prescribed dose, then treatment can begin using a final set of apertures.

In yet another aspect, one or more initial treatment parameters are provided. The initial treatment parameters are selected from a group consisting of a number of isotopic beams, isocenters for each isotopic beam, a prescribed dose for a target, a maximum dose for a critical structure, and one or more dose volume histogram constraints. Each of the isotopic beams are discretized into one or more beamlets. A cost for each of the one or more beamlets is computed. For each of the one or more beamlets, the beamlet is kept if the cost is greater than a threshold cost, and the beamlet is discarded if the cost is equal to or less than the threshold cost. A delivery sequence for the one or more kept beamlets is determined. The delivery sequence includes one or more apertures formed by a first set of one or more leaves and a second set of one or more leaves in a collimator. A dose value for each of the one or more apertures is calculated using an a priori dose calculation method. A beam-on-time value is determined for each of the one or more apertures. A first value of an objective function is calculated based on the determined beam-on-time values. For each of the one or more apertures, the aperture is discarded if the determined beam-on-time value is less than a beam-on-time threshold. The beam-on-time values for the one or more apertures that are not discarded are adjusted. A second value of the objective function is calculated based on the adjusted beam-on-time values. A determination is made as to whether the objective function has converged. This determination is based on a difference between the first value of the objective function and the second value of the objective function.

The above methods, apparatus, computer program products, and systems can, in some implementations, further include one or more of the following features.

The computing can be performed using a pre-computed influence matrix or by running a Monte Carlo simulation.

The threshold cost can be selected from the group consisting of a zero value, a predetermined fraction of a maximum cost for the one or more beamlets, and a predetermined fraction of the average cost for the one or more beamlets having a cost greater than zero.

The a priori dose calculation method can be selected from a group consisting of a Monte Carlo simulation and a discrete ordinates method.

The computing, the keeping, the discarding the beamlet, the determining the delivery sequence, the calculating the dose value, the determining the beam-on-time value, the calculating the first value of the objective function, the discarding the aperture, the adjusting the beam-on-time value, and the calculating the second value of the objective function can be repeated until the objective function has converged.

Determining whether the objective has converged can include comparing the first value of the objective function and the second value of the objective function in a current iteration with the first value of the objective function and the second value of the objective function in one or more previous iterations.

If the objective function has converged, then treatment can begin using a final set of apertures.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

Like reference symbols in the various drawings indicate like elements.

DETAILED DESCRIPTION

The subject matter disclosed herein relates to the development of an IMRT treatment delivery plan for a radiotherapy system that can mitigate the effects of undesired or unaccounted for radiation in the penumbra of an isotopic beam. In some implementations, these effects can be reduced by adjusting the apertures that are used to deliver the radiation doses.

Figure 1:
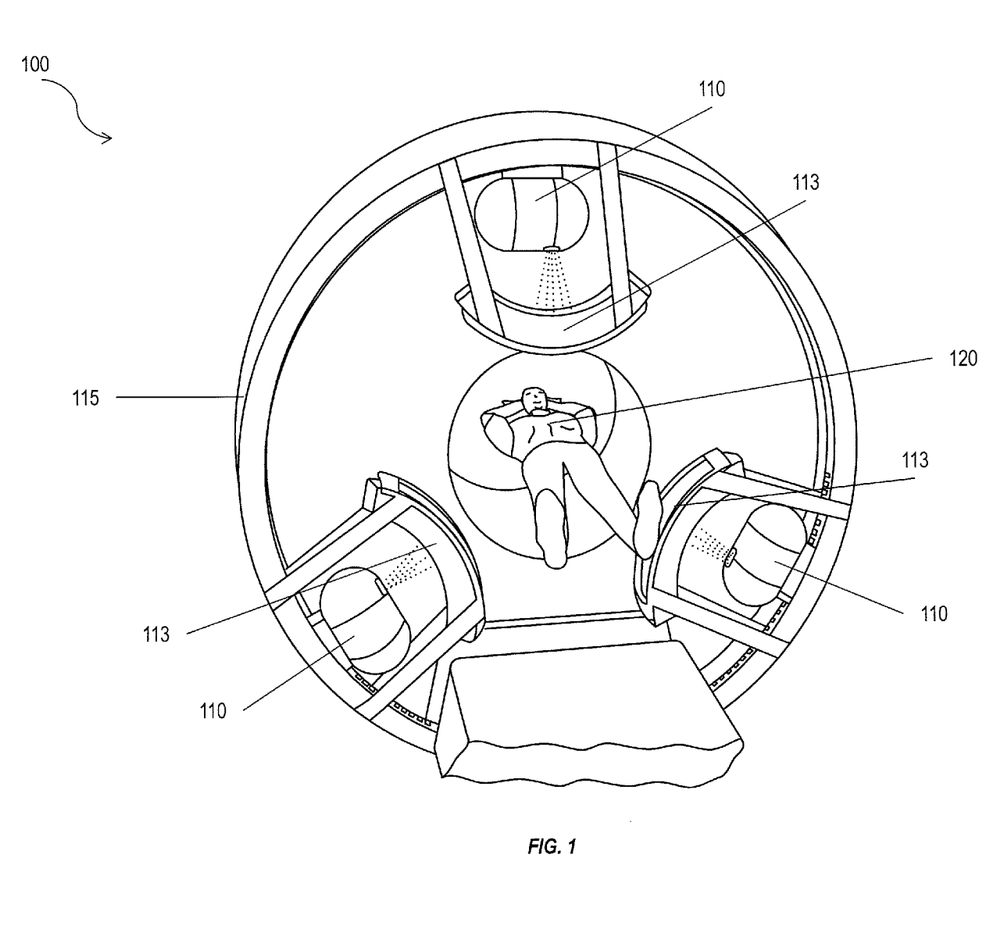
FIG. 1 illustrates a radiation therapy system.

FIG. 1 illustrates a radiation therapy system 100 that can perform IMRT. IMRT is a technique for shaping a radiotherapy beam (such as a Cobalt-60 beam) in accordance with the size, shape, and location of a tumor. Radiation therapy system 100 can include one or more isotopic radiation sources 110 (such as a Cobalt-60 radiation source) that project a beam toward patient 120 through multileaf collimator 113. Radiation source 110 and multileaf collimator 113 can be attached to gantry 115. During treatment, gantry 115 can rotate to different positions to enable irradiation from different angles. Although the configuration of FIG. 1 illustrates three radiation source-multileaf collimator pairs, any number of radiation source-multileaf collimator pairs can be used.

Figure 2:
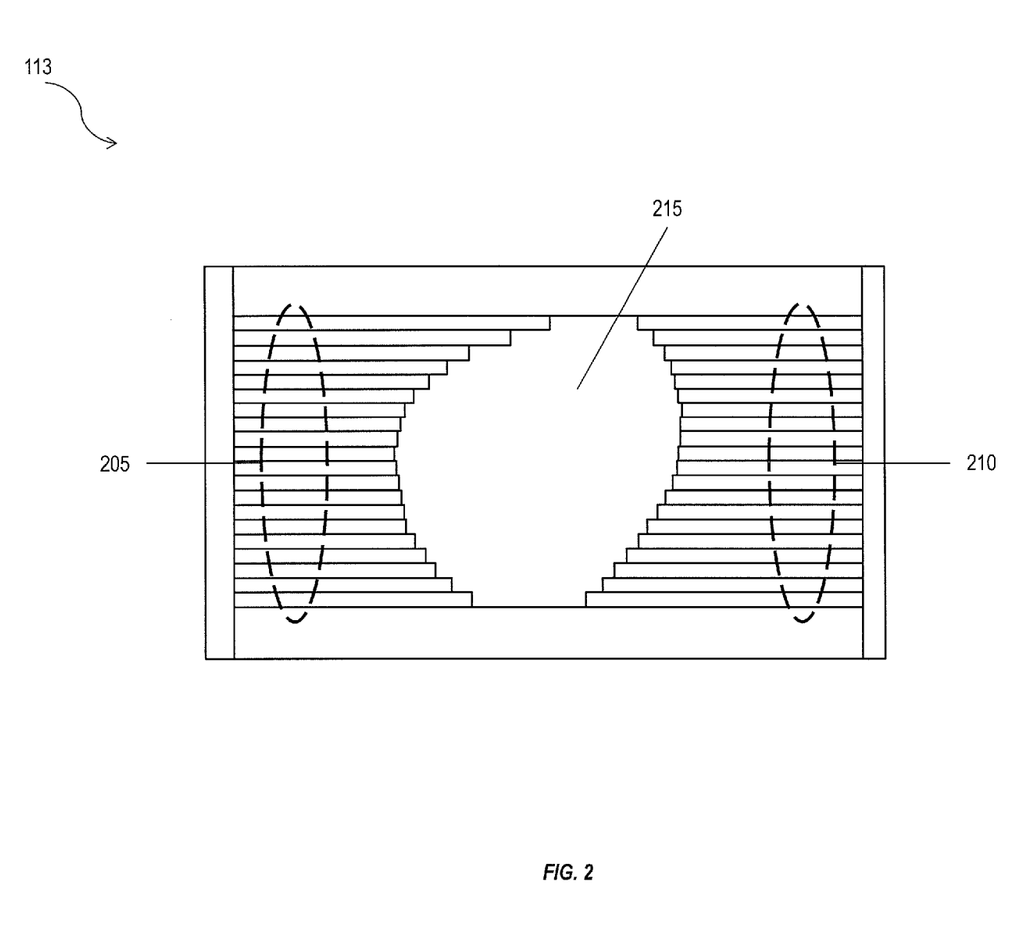
FIG. 2 illustrates a multileaf collimator.

FIG. 2 illustrates a magnified view of multileaf collimator 113. Multileaf collimator 113 can include a left bank of one or more leaves 205 and a right bank of one or more leaves 210. These leaves can be positioned on opposing sides of multileaf collimator 113 and controlled to open to form apertures 215 of varying sizes. The number of leaves in the left and right banks can vary.

A multileaf collimator control system can control the opposing banks of leaves 205 and 210 and independently position the edge of each leaf to a specified location in order to block a radiation beam and form a field size of a specific shape. The patterns formed by shifting leaves 205 and 210 can block parts of the beam that are transmitted from radiation source 110 which can shape or trim the isotopic beam. In some implementations, shifting leaves 205 and 210 can interdigitate such that leaves 205 crisscross past leaves 210 and vice versa. The control of these leaves is generally described in "Optimal Multileaf Collimator Leaf Sequencing In IMRT Treatment Planning," by Z. Taskin et al., Operations Research (2010), pp. 1-17, the contents of which are incorporated herein by reference in their entirety for all purposes.

An IMRT treatment plan can be developed before patient 120 is subjected to radiation. Treatment planning can use images acquired by 3-D computed tomography (CT), positron emission tomography (PET) and/or magnetic resonance imaging (MRI) in conjunction with computerized dose calculations in order to find out the beam cross section intensity pattern that will best conform the dose to the patient's individual target shape and location. These diagnostic images can help determine the precise location of the target prior to radiation sessions. The target can be, for example, a tumor.

A fluence map and delivery sequence can be developed during the treatment planning process. A fluence map can specify the intensity profile for the isotopic beams used during treatment. In order to enable delivery of the fluence map by the multileaf collimator, the fluence map can be converted into a set of deliverable apertures or segments that can be formed by the leaves in multileaf collimator 113. Leaves 205 and 210 can shift to form specific patterns, thereby blocking portions of the isotopic beams according to the intensity profile from the fluence map.

Figure 4:
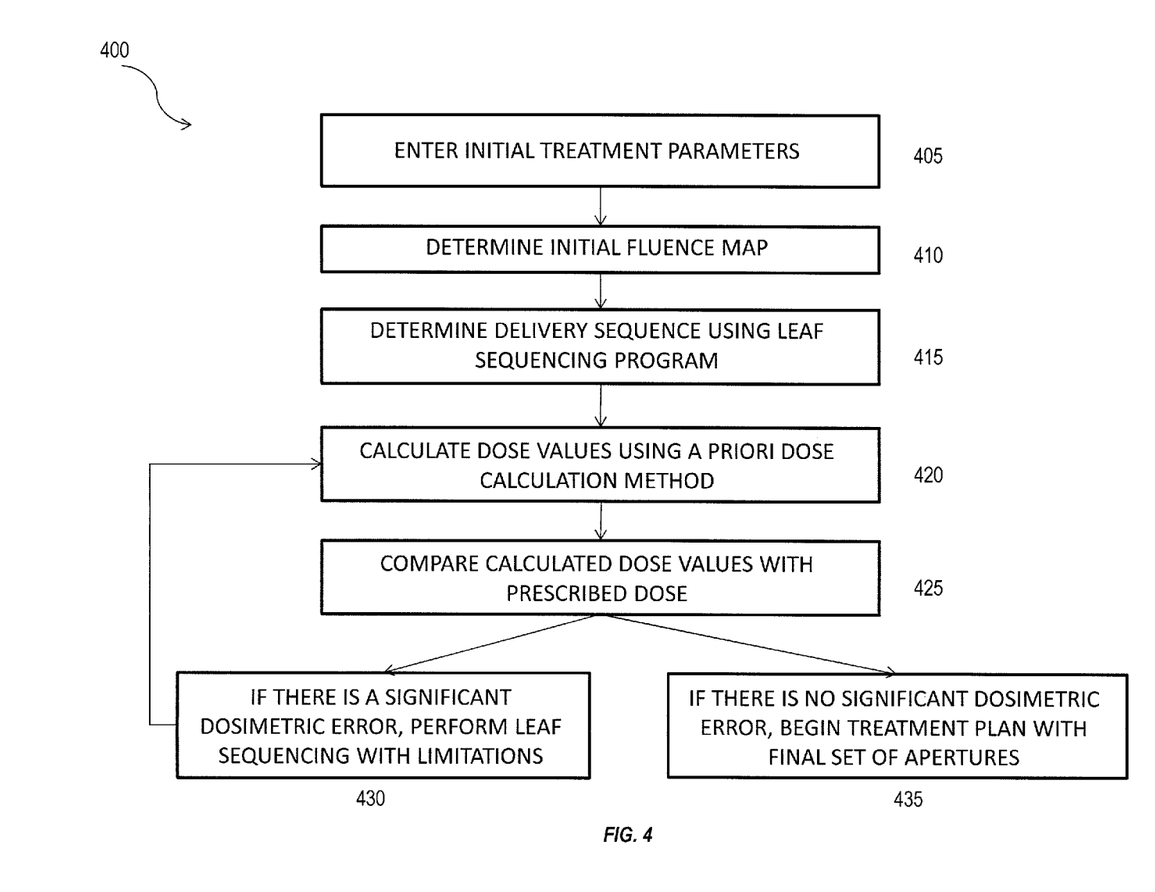
FIG. 4 illustrates another implementation for developing an IMRT treatment delivery plan.
Figure 5:
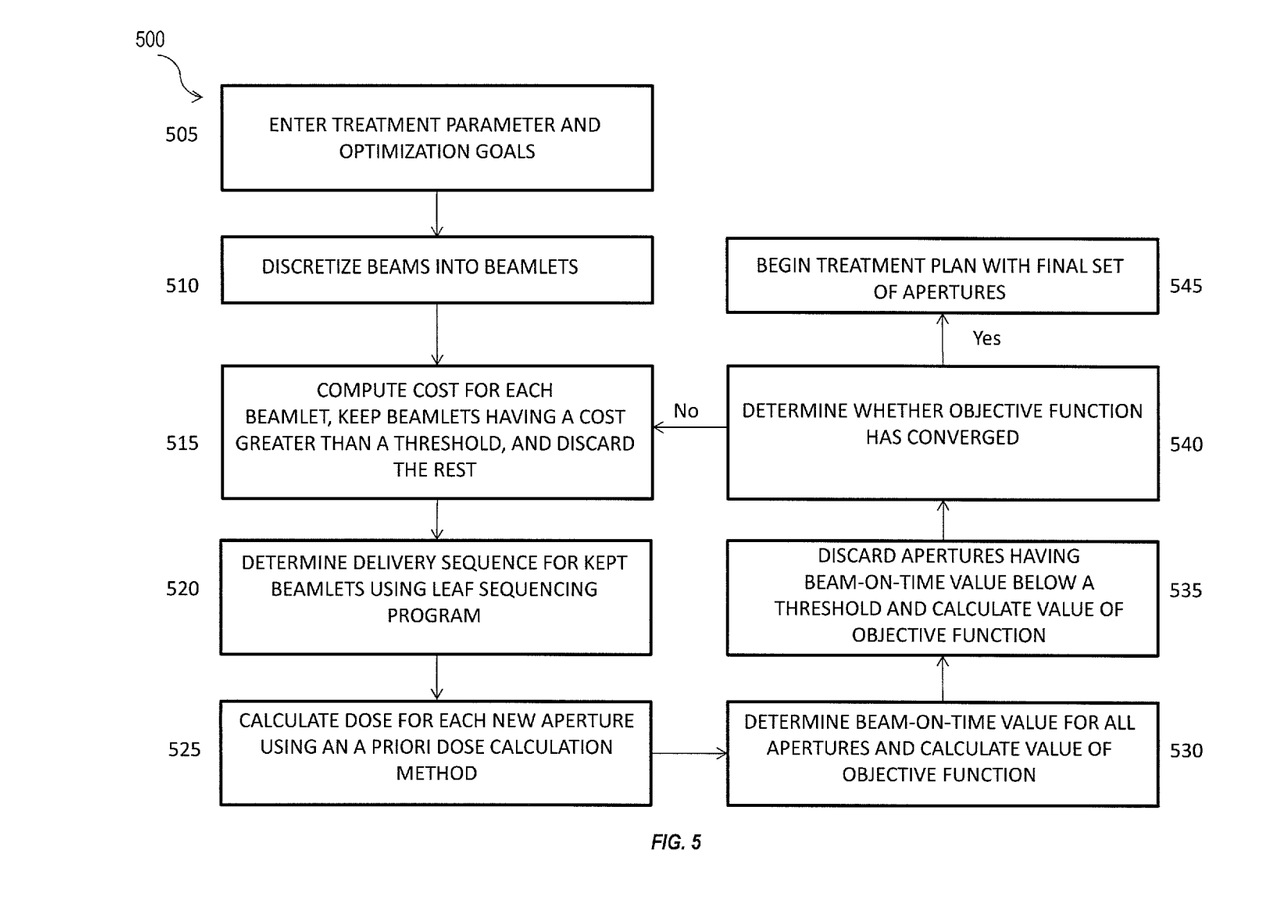
FIG. 5 illustrates yet another implementation for developing an IMRT treatment delivery plan.

As the size of the deliverable apertures or segments formed by leaves 205 and 210 increases in size, the beam edge or penumbra associated with the isotopic beam also increases in size. This effect is apparent, for example, when a Cobalt-60 beam is used, as the penumbra associated with this particular beam may not be as sharp as a linear accelerator beam, for example. Although penumbra in a linear accelerator beam also increases with field size, the effect is less significant than in a Cobalt-60 beam. Undesired or unaccounted for radiation in the penumbra of an isotopic beam can adversely impact critical structures near the target and the accurate delivery of a prescribed dose. The flowcharts illustrated in FIGS. 3-5 illustrate different implementations of an IMRT treatment plan that can mitigate this effect.

Figure 3:
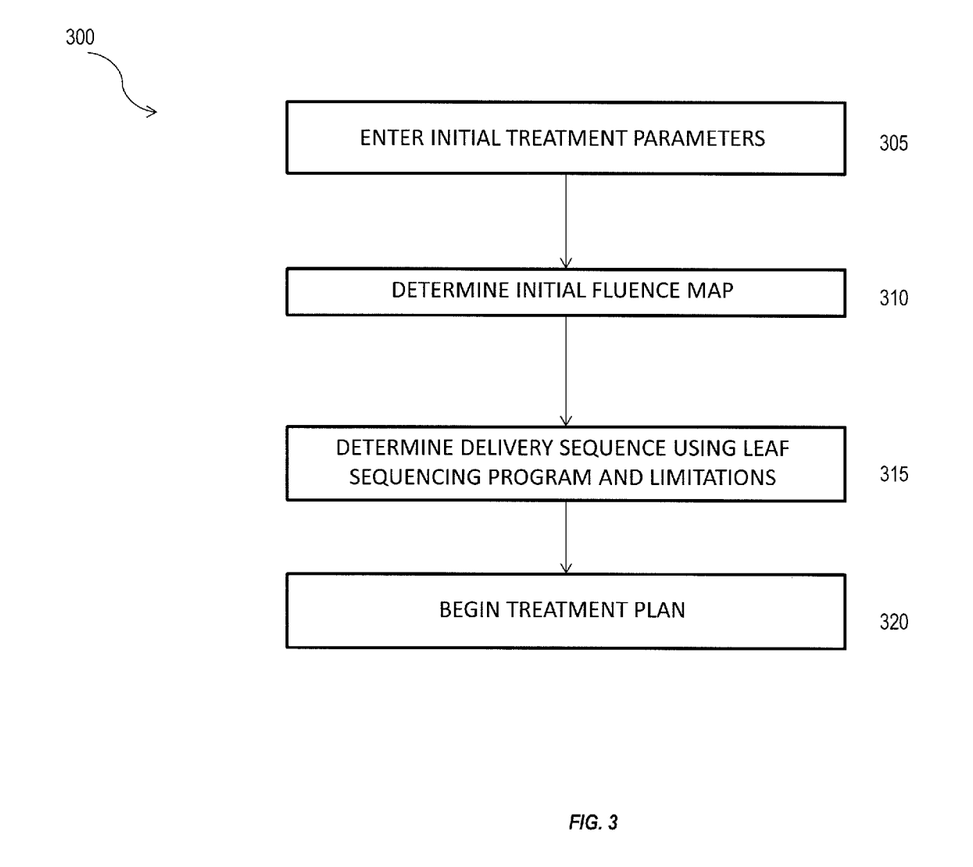
FIG. 3 illustrates an implementation for developing an IMRT treatment delivery plan.

FIG. 3 illustrates a flowchart 300 for IMRT treatment delivery plan development that can be used with radiation therapy system 100. At 305, initial treatment parameters can be entered. These parameters can define various operational parameters and optimization objectives for a given treatment plan. The initial treatment parameters can include, for example, the number of beams (e.g., the number of Cobalt-60 beams) to be used, the isocenters for each beam, the prescribed dose for the target, the minimum dose for the target, target dose uniformity requirements, generalized equivalent uniform dose requirements for target and critical structures, the maximum and mean doses to critical structures, various biological objectives (tumor control probability, normal tissue complication probability, etc.), dose volume histogram constraints, and the like. Dose volume histogram constraints can include penalty functions that specify the relative importance of sparing various critical structures and providing a requested target dose. A beam angle can also be included with these initial treatment parameters. The beam angle can specify, for example, the angle of rotation of the beam relative to the gantry or relative to the patient (when the multi-leaf collimator or the couch on which the patient is lying on is tilted).

At 310, an initial fluence map can be determined based on the initial treatment parameters. The initial fluence map can be computed using, for example, a fluence map optimization program. An isotopic beam may be abstractly represented by one or more beamlets. The initial fluence map can contain the fluence values for these beamlets.

At 315, a delivery sequence can be determined using a leaf sequencing program. The leaf sequencing program can formulate a set of deliverable apertures for the fluence values in the initial fluence map. These apertures can be determined, for example, by solving a combinatorial optimization model. This model can optimize the solution based on various treatment criteria including, for example, the total beam-on-time (i.e., the amount of time that the patient is irradiated) and the total delivery time (i.e., the total beam-on-time plus the amount of time that the multileaf collimator spends shaping the apertures and the amount of time needed to rotate the gantry to the desired beam angles).

In order to reduce radiation in the penumbra of the isotopic beam, limitations can be imposed on the apertures determined by the leaf sequencing program. These limitations can, for example, specify an aperture size that is constrained to be substantially less than a maximum aperture size allowed by the dimensions of the multileaf collimator. Limiting the aperture size formed by the leaves of the collimator can trim the isotopic beam which, in turn, can reduce the size of the associated penumbra. The aperture size can, for example, be restricted to a maximum area of substantially 2 cm by 2 cm, substantially 1 cm by 1 cm, and the like. In some implementations, the constraints on aperture size can apply only when the isotopic beam is close to a critical structure. This can occur, for example, when the beam penumbra is close enough to hit the critical structure. When the distance between the beam penumbra and a critical structure is large enough such that there is no overlap, the constraints on aperture size can be removed. Removing these constraints can enable the delivery of a large dose of radiation to the target without fear of hitting a critical structure and can allow for faster treatment. Other limitations can be used including, for example, specifying a maximum number of apertures to improve delivery time, specifying a minimum distance between leaves, prohibiting leaf interdigitation, using apertures that reduce the tongue and groove effect between leaves, imposing a minimum beam-on-time for each aperture to reduce any uncertainty associated with the delivery of very short beams, and the like. These limitations can be applied in any order and in any combination.

At 320, radiation therapy system 100 can begin its treatment plan in accordance with the fluence values determined at 310 and the delivery sequence determined at 315.

FIG. 4 illustrates a flowchart 400 of another implementation of IMRT treatment delivery plan development that can be used with radiation therapy system 100. Initial treatment parameters can be entered at 405. These initial treatment parameters can include, for example, the number of isotopic beams to be used, the transmission angle for each beam, the prescribed dose for a target, dose volume histogram constraints, and the like. An initial fluence map can be determined at 410. Processes 405 and 410 can proceed in the same manner as processes 305 and 310.

At 415, the leaf sequencer can determine a delivery sequence for the initial fluence map determined at 410. Process 415 can proceed in a similar manner as process 315. However, unlike process 315, the leaf sequencer may or may not impose any limitations on the apertures formed by the multileaf collimator.

At 420, the dose values associated with the beam shapes formed by the multileaf collimator can be calculated using an a priori dose calculation method. Various calculation techniques can be used including, for example, a Monte Carlo simulation, a discrete ordinates method, and the like. These techniques can accurately account for radiation in the penumbra of the isotopic beams borne from the apertures determined by the leaf sequencer.

At 425, the dose values calculated at 420 can be compared with the prescribed dose entered at 405. If a significant dosimetric error between the calculated dose and the prescribed dose is observed, then control can proceed to 430.

At 430, the leaf sequencer can determine a new set of deliverable apertures. The leaf sequencing performed at 430 may include one or more of the limitations described above with respect to process 315. These limitations can be applied in any order and in any combination.

Once the new set of deliverable apertures is determined at 430, control can return to 420, and dose values associated with the new apertures can be computed using an a priori dose calculation method as described above. As illustrated in FIG. 4, processes 420-430 can repeat until there is no significant dosimetric error between the calculated dose and the prescribed dose. When there is no such error, control can proceed to 435, and radiation therapy system 100 can begin its treatment plan using the final set of apertures. The final set of apertures can be determined from the most recent iteration of flowchart 400 and can correspond to the apertures determined either at 415 or 430, for example.

FIG. 5 illustrates a flowchart 500 of yet another implementation of IMRT treatment delivery plan development that can be used with radiation therapy system 100. This implementation can define the treatment plan in terms of apertures (rather than beamlets and their associated intensities) and builds on the approach described in "A Column Generation Approach To Radiation Therapy Treatment Planning Using Aperture Modulation," by H. Romeijn et al., Society For Industrial And Applied Mathematics, Vol. 15, No. 3 (2005), pp. 838-862, the contents of which are incorporated herein by reference in their entirety for all purposes.

At 505, initial treatment parameters can be entered as described above with respect to 305 and 405. In addition, optimization goals can be formulated in terms of an objective function $F(D_i)$. The objective function can depend on a dose $D_i$ that is deposited in a particular voxel i in the region to be irradiated.

At 510, the beams to be used during treatment can be discretized into a set of beamlets. The size of the beamlets in the direction of the leaves can be set by the leaf width. Any beamlet size can be used in the direction along the leaves including uniform or non-uniform beamlet sizes.

At 515, the cost $c_j$ for a beamlet j can be determined using, for example, a pre-computed influence matrix $d_{ij}$. This matrix can provide the dose that is deposited into a voxel i by a beamlet j. The cost $c_j$ can be calculated according to the following equation:

$$c_j = -\Sigma_i d_{ij} \partial F/\partial D_i.$$

Alternatively, $c_j$ can be calculated by running a Monte Carlo simulation and accumulating the energy deposited from particles passing through the area of beamlet j weighted with $\partial F/\partial D_i$. The term $\partial F/\partial D_i$ is the partial derivative of the objective function $F(D_i)$ with respect to the dose in voxel i.

Once the cost $c_j$ is determined for each beamlet, only beamlets having a cost above a certain threshold can be kept while all other beamlets can be discarded (i.e., beamlets having a cost equal to or less than the threshold). This threshold can be a predetermined value including, for example, zero (i.e., all beamlets that improve the objective function are kept), a predetermined fraction of the maximum cost $c_j$ for all of the beamlets, a predetermined fraction of the average cost for all beamlets having a cost $c_j > 0$, and the like.

At 520, a delivery sequence can be determined for the kept beamlets using a leaf sequencing program. This delivery sequence can include one or more apertures. These apertures can be determined with or without the limitations described above with respect to 315. These apertures can include all newly created apertures, the addition of only a single aperture having the maximum influence on the objective function, or the addition of a subset of the newly created apertures. The subset of apertures can be selected based on each aperture's influence on the objective function.

At 525, the dose from each newly added aperture can be computed using an a priori dose calculation method such as a Monte Carlo simulation, a discrete ordinates method, and the like.

At 530, the weight or beam-on-time value for all apertures (i.e., pre-existing and newly added apertures) can be determined using an optimization program. These determinations can be made in order to optimize the objective function. A value of the objective function can be calculated based on the determined beam-on-time values.

At 535, apertures having a beam-on-time value below a certain threshold can be discarded. If, however, all apertures have a beam-on-time value that meets or exceeds the threshold and the predetermined maximum number of apertures has been reached, then apertures having the lowest influence on the value of the objective function can be discarded. The weights or beam-on-time values for the remaining apertures can be adjusted in order to optimize the objective function, and a value of the objective function can be calculated based on these adjusted beam-on-time values.

At 540, a determination can be made as to whether the objective function has converged. This determination can be made by comparing the objective function values obtained at 530 and 535 during the current iteration with the objective function values obtained in previous iterations (i.e., when control loops through 515-540). If, for example, the change in objective function value is less than a particular threshold for a given number of iterations, then the objective function has converged, and the treatment plan can begin at 545 using the final set of apertures. The final set of apertures can be determined from the most recent iteration of flowchart 500 and can correspond to the apertures that have not been discarded by process 535. If, however, the change in objective function value is equal to or greater than the threshold for a given number of iterations, then the objective function has not converged and control can loop back to 515 to determine a new set of apertures as described above. In some implementations, control can proceed from 540 to 545 when all input clinical objectives have been satisfied.

As described above with respect to FIG. 5, the size of the initial apertures (which can be large) can gradually decrease as control iterates through 515-540. This gradual decrease in aperture size combined with the ability to discard apertures can improve the dose distribution as specified by the objective function.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

What is claimed is:

1. A method comprising:
providing one or more initial treatment parameters selected from a group consisting of a number of isotopic beams, isocenters for each isotopic beam, a prescribed dose for a target, a maximum dose for a critical structure, and one or more dose volume histogram constraints;
determining an initial fluence map including one or more beamlets, the initial fluence map specifying a fluence value for each of the one or more beamlets; and
determining a delivery sequence for the fluence values in the initial fluence map, the delivery sequence including one or more apertures formed by a first set of one or more leaves and a second set of one or more leaves in a collimator, the one or more apertures having a specified size constrained to substantially less than a maximum size associated with the collimator, when the isotopic beam is near the critical structure.

2. The method of claim 1, wherein the specified size is substantially 2 centimeters by 2 centimeters or less.

3. The method of claim 1, wherein the delivery sequence further specifies a maximum number of apertures or prohibits interdigitation between the first set of one or more leaves and the second set of one or more leaves.

4. The method of claim 1, further comprising:
beginning treatment based on the determined initial fluence map and the determined delivery sequence.

5. A method comprising:
providing one or more initial treatment parameters selected from a group consisting of a number of isotopic beams, isocenters for each isotopic beam, a prescribed dose for a target, a maximum dose for a critical structure, and one or more dose volume histogram constraints;
determining an initial fluence map including one or more beamlets, the initial fluence map specifying a fluence value for each of the one or more beamlets;
determining a first delivery sequence for the fluence values in the initial fluence map, the first delivery sequence including one or more apertures formed by a first set of one or more leaves and a second set of one or more leaves in a collimator;
calculating one or more dose values based on the one or more apertures in the first delivery sequence using an a priori dose calculation method;
comparing the one or more calculated dose values with the prescribed dose; and
determining a second delivery sequence if there is a significant error between the one or more calculated dose values and the prescribed dose.

6. The method of claim 5, wherein the second delivery sequence comprises one or more apertures formed by the first set of one or more leaves and the second set of one or more leaves, and
wherein the one or more apertures in the second delivery sequence have a specified size constrained to substantially less than a maximum size associated with the collimator, when the isotopic beam is near the critical structure.

7. The method of claim 6, wherein the second delivery sequence further specifies a maximum number of apertures or prohibits interdigitation between the first set of one or more leaves and the second set of one or more leaves.

8. The method of claim 6, wherein the specified size is substantially 2 centimeters by 2 centimeters or less.

9. The method of claim 5, wherein the a priori dose calculation method is selected from a group consisting of a Monte Carlo simulation and a discrete ordinates method.

10. The method of claim 5, further comprising:
beginning treatment using a final set of apertures if there is no significant error between the one or more calculated dose values and the prescribed dose.

11. A method comprising:
providing one or more initial treatment parameters selected from a group consisting of a number of isotopic beams, isocenters for each isotopic beam, a prescribed dose for a target, a maximum dose for a critical structure, and one or more dose volume histogram constraints;
discretizing each of the isotopic beams into one or more beamlets;
computing a cost for each of the one or more beamlets;
for each of the one or more beamlets, keeping the beamlet if the cost is greater than a threshold cost and discarding the beamlet if the cost is equal to or less than the threshold cost;
determining a delivery sequence for the one or more kept beamlets, the delivery sequence including one or more apertures formed by a first set of one or more leaves and a second set of one or more leaves in a collimator;
calculating a dose value for each of the one or more apertures using an a priori dose calculation method;
determining a beam-on-time value for each of the one or more apertures;
calculating a first value of an objective function based on the determined beam-on-time values;
for each of the one or more apertures, discarding the aperture if the determined beam-on-time value is less than a beam-on-time threshold;
adjusting the beam-on-time value for the one or more apertures that are not discarded;
calculating a second value of the objective function based on the adjusted beam-on-time values; and
determining whether the objective function has converged based on a difference between the first value of the objective function and the second value of the objective function.

12. The method of claim 11, wherein the computing is performed using a pre-computed influence matrix or by running a Monte Carlo simulation.

13. The method of claim 11, wherein the threshold cost is selected from the group consisting of a zero value, a predetermined fraction of a maximum cost for the one or more beamlets, and a predetermined fraction of the average cost for the one or more beamlets having a cost greater than zero.

14. The method of claim 11, wherein the a priori dose calculation method is selected from a group consisting of a Monte Carlo simulation and a discrete ordinates method.

15. The method of claim 11, further comprising:
repeating the computing, the keeping, the discarding the beamlet, the determining the delivery sequence, the calculating the dose value, the determining the beam-on-time value, the calculating the first value of the objective function, the discarding the aperture, the adjusting the beam-on-time value, and the calculating the second value of the objective function until the objective function has converged.

16. The method of claim 11, wherein the determining whether the objective has converged comprises comparing the first value of the objective function and the second value of the objective function in a current iteration with the first value of the objective function and the second value of the objective function in one or more previous iterations.

17. The method of claim 11, further comprising:
beginning treatment using a final set of apertures if the objective function has converged.

18. A system comprising:
a processor; and
a memory, wherein the processor and the memory are configured to perform operations comprising:
providing one or more initial treatment parameters selected from group consisting of a number of isotopic beams, isocenters for each isotopic beam, a prescribed dose for a target, a maximum dose for a critical structure, and one or more dose volume histogram constraints;
determining an initial fluence map including one or more beamlets, the initial fluence map specifying a fluence value for each of the one or more beamlets; and
determining a delivery sequence for the fluence values in the initial fluence map, the delivery sequence including one or more apertures formed by a first set of one or more leaves and a second set of one or more leaves in a collimator, the one or more apertures having a specified size constrained to substantially less than a maximum size associated with the collimator, when the isotopic beam is near the critical structure.

19. The system of claim 18, wherein the specified size is substantially 2 centimeters by 2 centimeters or less.

20. The system of claim 18, wherein the delivery sequence further specifies a maximum number of apertures or prohibits interdigitation between the first set of one or more leaves and the second set of one or more leaves.

21. The system of claim 18, the operations further comprising:
beginning treatment based on the determined initial fluence map and the determined delivery sequence.

22. A system comprising:
a processor; and
a memory, wherein the processor and the memory are configured to perform operations comprising:
providing one or more initial treatment parameters selected from a group consisting of a number of isotopic beams, isocenters for each isotopic beam, a prescribed dose for a target, a maximum dose for a critical structure, and one or more dose volume histogram constraints;
determining an initial fluence map including one or more beamlets, the initial fluence map specifying a fluence value for each of the one or more beamlets;
determining a first delivery sequence for the fluence values in the initial fluence map, the first delivery sequence including one or more apertures formed by a first set of one or more leaves and a second set of one or more leaves in a collimator;
calculating one or more dose values based on the one or more apertures in the first delivery sequence using an a priori dose calculation method;
comparing the one or more calculated dose values with the prescribed dose; and
determining a second delivery sequence if there is a significant error between the one or more calculated dose values and the prescribed dose.

23. The system of claim 22, wherein the second delivery sequence comprises one or more apertures formed by the first set of one or more leaves and the second set of one or more leaves, and
wherein the one or more apertures in the second delivery sequence have a specified size constrained to substantially less than a maximum size associated with the collimator, when the isotopic beam is near the critical structure.

24. The system of claim 23, wherein the second delivery sequence further specifies a maximum number of apertures or prohibits interdigitation between the first set of one or more leaves and the second set of one or more leaves.

25. The system of claim 23, wherein the specified size is substantially 2 centimeters by 2 centimeters or less.

26. The system of claim 22, wherein the a priori dose calculation method is selected from a group consisting of a Monte Carlo simulation and a discrete ordinates method.

27. The system of claim 22, the operations further comprising:
beginning treatment using a final set of apertures if there is no significant error between the one or more calculated dose values and the prescribed dose.

28. A system comprising:
a processor; and
a memory, wherein the processor and the memory are configured to perform operations comprising:
providing one or more initial treatment parameters selected from a group consisting of a number of isotopic beams, isocenters for each isotopic beam, a prescribed dose for a target, a maximum dose for a critical structure, and one or more dose volume histogram constraints;
discretizing each of the isotopic beams into one or more beamlets;
computing a cost for each of the one or more beamlets;
for each of the one or more beamlets, keeping the beamlet if the cost is greater than a threshold cost and discarding the beamlet if the cost is equal to or less than the threshold cost;
determining a delivery sequence for the one or more kept beamlets, the delivery sequence including one or more apertures formed by a first set of one or more leaves and a second set of one or more leaves in a collimator;
calculating a dose value for each of the one or more apertures using an a priori dose calculation method;
determining a beam-on-time value for each of the one or more apertures;
calculating a first value of an objective function based on the determined beam-on-time values;
for each of the one or more apertures, discarding the aperture if the determined beam-on-time value is less than a beam-on-time threshold;
adjusting the beam-on-time value for the one or more apertures that are not discarded;

calculating a second value of the objective function based on the adjusted beam-on-time values; and determining whether the objective function has converged based on a difference between the first value of the objective function and the second value of the objective function.

29. The system of claim 28, wherein the computing is performed using a pre-computed influence matrix or by running a Monte Carlo simulation.

30. The system of claim 28, wherein the threshold cost is selected from the group consisting of a zero value, a predetermined fraction of a maximum cost for the one or more beamlets, and a predetermined fraction of the average cost for the one or more beamlets having a cost greater than zero.

31. The system of claim 28, wherein the a priori dose calculation method is selected from a group consisting of a Monte Carlo simulation and a discrete ordinates method.

32. The system of claim 28, the operations further comprising:

repeating the computing, the keeping, the discarding the beamlet, the determining the delivery sequence, the calculating the dose value, the determining the beam-on-time value, the calculating the first value of the objective function, the discarding the aperture, the adjusting the beam-on-time value, and the calculating the second value of the objective function until the objective function has converged.

33. The system of claim 28, wherein the determining whether the objective has converged comprises comparing the first value of the objective function and the second value of the objective function in a current iteration with the first value of the objective function and the second value of the objective function in one or more previous iterations.

34. The system of claim 28, the operations further comprising:

beginning treatment using a final set of apertures if the objective function has converged.

35. A non-transitory computer-readable medium containing instructions to configure a processor to perform operations comprising:

providing one or more initial treatment parameters selected from a group consisting of a number of isotopic beams, isocenters for each isotopic beam, a prescribed dose for a target, a maximum dose for a critical structure, and one or more dose volume histogram constraints;

determining an initial fluence map including one or more beamlets, the initial fluence map specifying a fluence value for each of the one or more beamlets; and determining a delivery sequence for the fluence values in the initial fluence map, the delivery sequence including one or more apertures formed by a first set of one or more leaves and a second set of one or more leaves in a collimator, the one or more apertures having a specified size constrained to substantially less than a maximum size associated with the collimator, when the isotopic beam is near the critical structure.

36. A non-transitory computer-readable medium containing instructions to configure a processor to perform operations comprising:

providing one or more initial treatment parameters selected from a group consisting of a number of isotopic beams, isocenters for each isotopic beam, a prescribed dose for a target, a maximum dose for a critical structure, and one or more dose volume histogram constraints;

determining an initial fluence map including one or more beamlets, the initial fluence map specifying a fluence value for each of the one or more beamlets;

determining a first delivery sequence for the fluence values in the initial fluence map, the first delivery sequence including one or more apertures formed by a first set of one or more leaves and a second set of one or more leaves in a collimator;

calculating one or more dose values based on the one or more apertures in the first delivery sequence using an a priori dose calculation method;

comparing the one or more calculated dose values with the prescribed dose; and determining a second delivery sequence if there is a significant error between the one or more calculated dose values and the prescribed dose.

37. A non-transitory computer-readable medium containing instructions to configure a processor to perform operations comprising:

providing one or more initial treatment parameters selected from a group consisting of a number of isotopic beams, isocenters for each isotopic beam, a prescribed dose for a target, a maximum dose for a critical structure, and one or more dose volume histogram constraints;

discretizing each of the isotopic beams into one or more beamlets;

computing a cost for each of the one or more beamlets;

for each of the one or more beamlets, keeping the beamlet if the cost is greater than a threshold cost and discarding the beamlet if the cost is equal to or less than the threshold cost;

determining a delivery sequence for the one or more kept beamlets, the delivery sequence including one or more apertures formed by a first set of one or more leaves and a second set of one or more leaves in a collimator;

calculating a dose value for each of the one or more apertures using an a priori dose calculation method;

determining a beam-on-time value for each of the one or more apertures;

calculating a first value of an objective function based on the determined beam-on-time values;

for each of the one or more apertures, discarding the aperture if the determined beam-on-time value is less than a beam-on-time threshold;

adjusting the beam-on-time value for the one or more apertures that are not discarded;

calculating a second value of the objective function based on the adjusted beam-on-time values; and determining whether the objective function has converged based on a difference between the first value of the objective function and the second value of the objective function.

* * * * *